(12) United States Patent
Portney

(10) Patent No.: US 11,719,958 B2
(45) Date of Patent: Aug. 8, 2023

(54) MULTI-CHAMBER SWITCHABLE OPTICAL ELEMENT

(71) Applicant: Valdemar Portney, Newport Coast, CA (US)

(72) Inventor: Valdemar Portney, Newport Coast, CA (US)

( * ) Notice: Subject to any disclaimer, the term of this patent is extended or adjusted under 35 U.S.C. 154(b) by 389 days.

(21) Appl. No.: 16/948,924

(22) Filed: Oct. 6, 2020

(65) Prior Publication Data

US 2021/0240010 A1 Aug. 5, 2021

Related U.S. Application Data

(60) Provisional application No. 62/970,100, filed on Feb. 4, 2020.

(51) Int. Cl.
*G02C 7/08* (2006.01)
*G02C 7/06* (2006.01)
*A61F 2/16* (2006.01)

(52) U.S. Cl.
CPC ............ *G02C 7/085* (2013.01); *A61F 2/1635* (2013.01); *G02C 7/06* (2013.01); *G02C 7/083* (2013.01); *A61F 2250/0003* (2013.01)

(58) Field of Classification Search
CPC .......... G02C 7/085; G02C 7/06; G02C 7/083; G02C 2202/20; G02C 7/041; A61F 2250/0003; A61F 2/1635
See application file for complete search history.

(56) References Cited

U.S. PATENT DOCUMENTS

| | | | |
|---|---|---|---|
| 6,857,741 B2 | 2/2005 | Blum et al. | |
| 8,500,805 B2 | 8/2013 | Kobayashi et al. | |
| 8,523,354 B2 | 9/2013 | Haddock et al. | |
| 9,364,319 B2 | 6/2016 | Portney | |
| 2009/0256977 A1* | 10/2009 | Haddock | B29D 11/00817 156/60 |
| 2010/0066973 A1* | 3/2010 | Portney | A61F 2/1618 351/159.05 |
| 2011/0116035 A1 | 5/2011 | Fritsch et al. | |

(Continued)

FOREIGN PATENT DOCUMENTS

WO 2018/222357 A1 12/2018

*Primary Examiner* — Mustak Choudhury
(74) *Attorney, Agent, or Firm* — Orbit IP

(57) ABSTRACT

A lens includes a switchable optical element having an optical substrate with a diffraction surface. A substrate cover forms an internal chamber with the optical substrate. An elastic membrane in contact with the diffraction surface of the substrate forms an active chamber. Through channels are placed through the optical substrate's thinnest parts of the grooves connecting the active and internal chambers. The switchable optical element changes focus positions between one focus with the optical fluid filling the active chamber and the elastic membrane taking a non-periodic shape with the membrane's surface forming a refractive shape of certain curvature and another focus where the optical fluid is transported from the active chamber through the through channels to the internal chamber for the elastic membrane to conform to the diffraction surface shape of the optical substrate with the membrane's surface forming diffractive surface of periodicity of the diffractive guiding surface.

21 Claims, 8 Drawing Sheets

(56) References Cited

U.S. PATENT DOCUMENTS

| | | | |
|---|---|---|---|
| 2012/0140167 A1* | 6/2012 | Blum | G02C 7/04 |
| | | | 351/159.73 |
| 2014/0085726 A1* | 3/2014 | Portney | G02C 7/083 |
| | | | 351/159.01 |
| 2018/0173010 A1* | 6/2018 | Harant | G02C 7/049 |
| 2018/0188558 A1* | 7/2018 | Portney | G02C 7/081 |
| 2019/0339509 A1 | 1/2019 | Chuang et al. | |
| 2019/0049749 A1* | 2/2019 | Payor | G02C 7/028 |
| 2019/0159890 A1* | 5/2019 | Salahieh | A61F 2/1635 |
| 2020/0008931 A1* | 1/2020 | Argento | A61F 2/1635 |

* cited by examiner

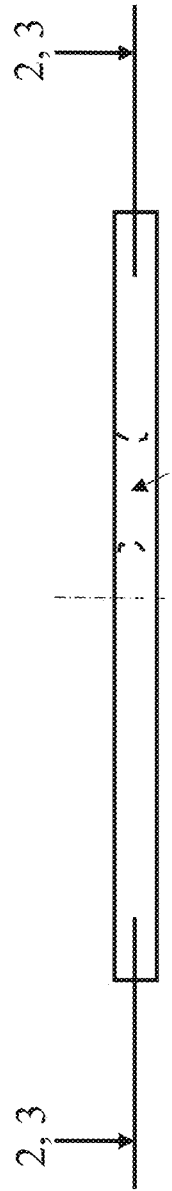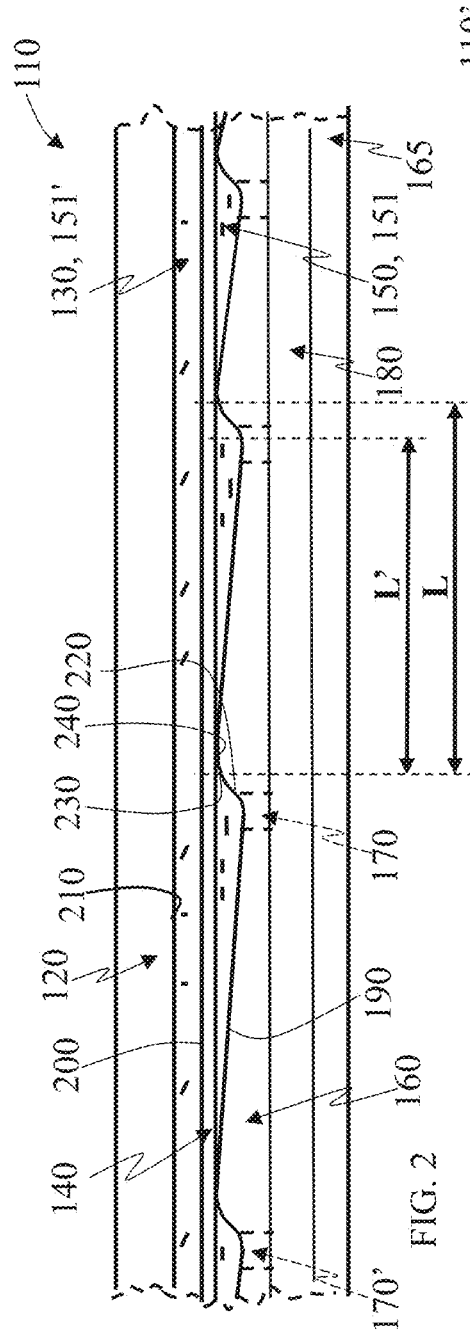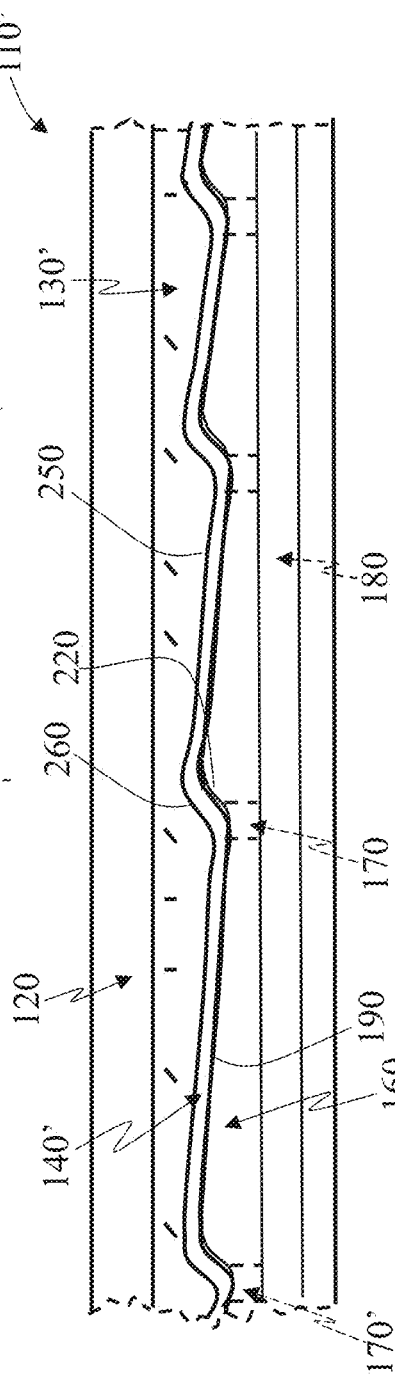

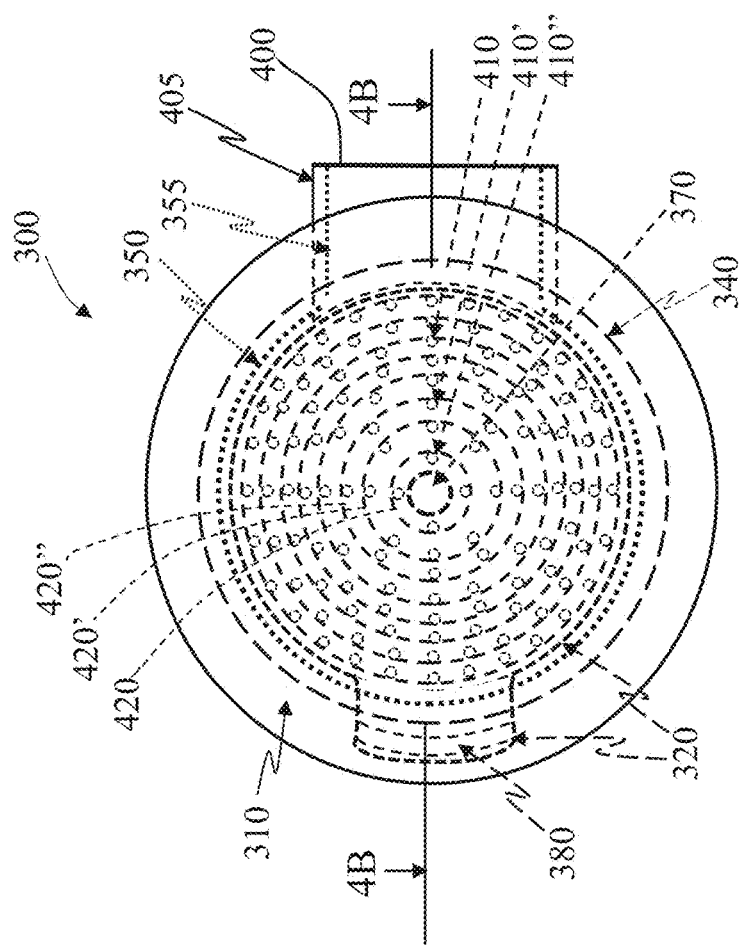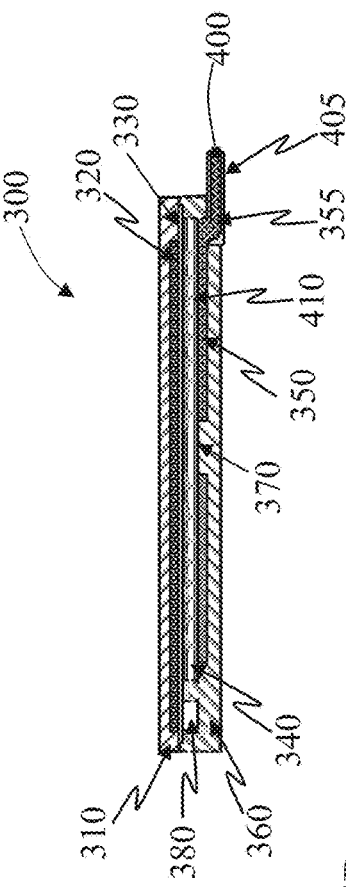
FIG. 4A
FIG. 4B

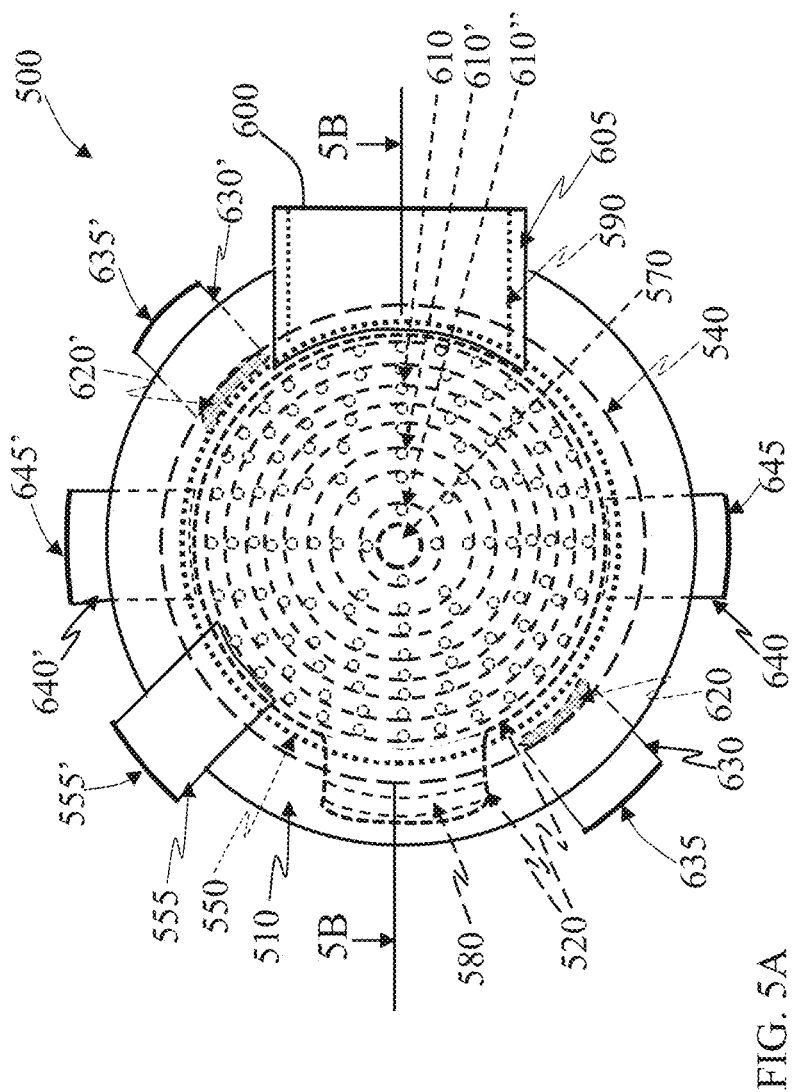
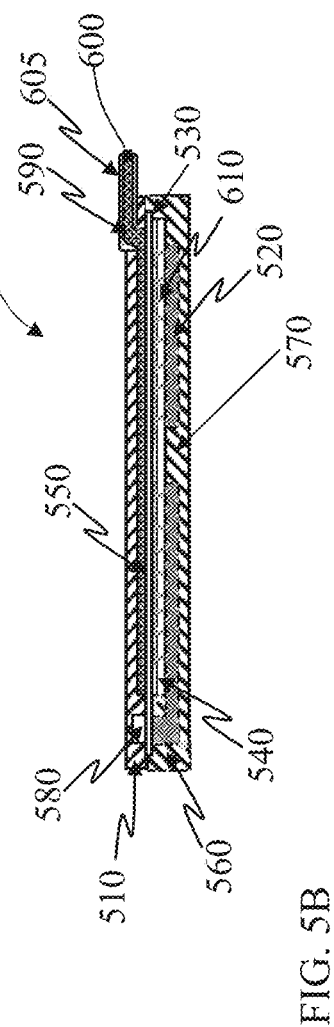
FIG. 5A
FIG. 5B

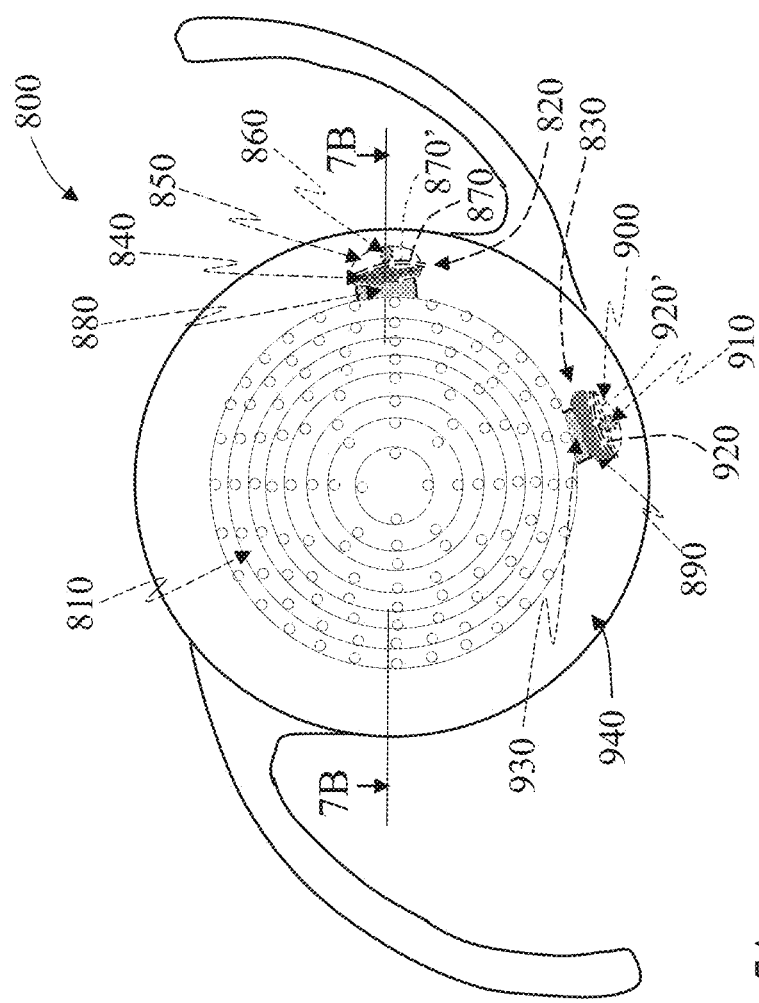
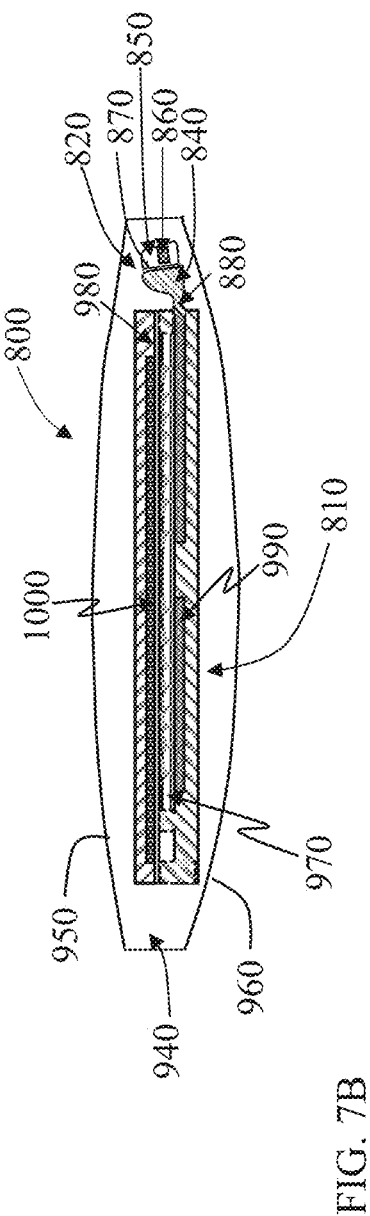
FIG. 7A
FIG. 7B

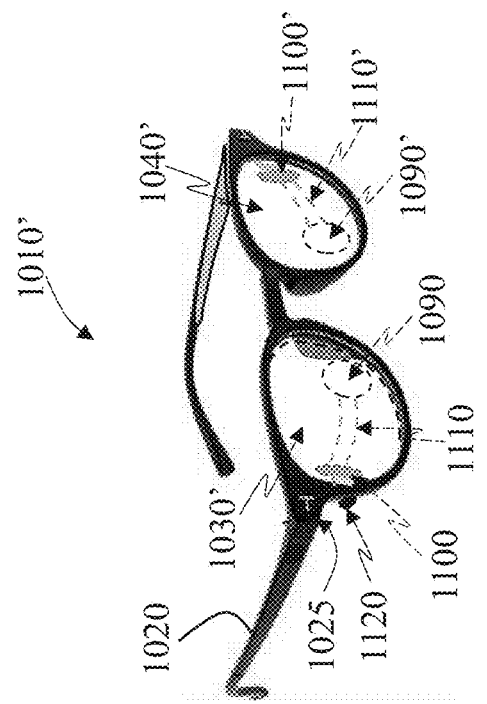
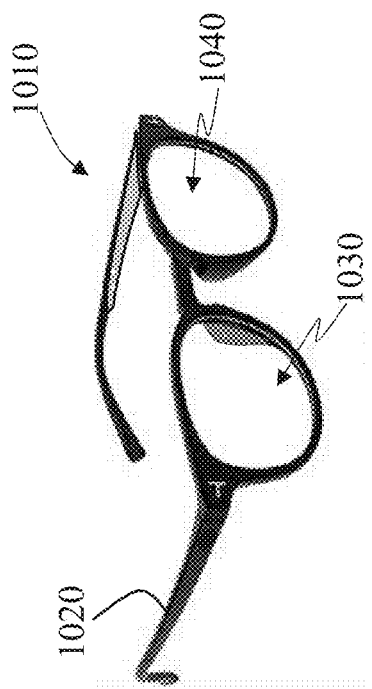
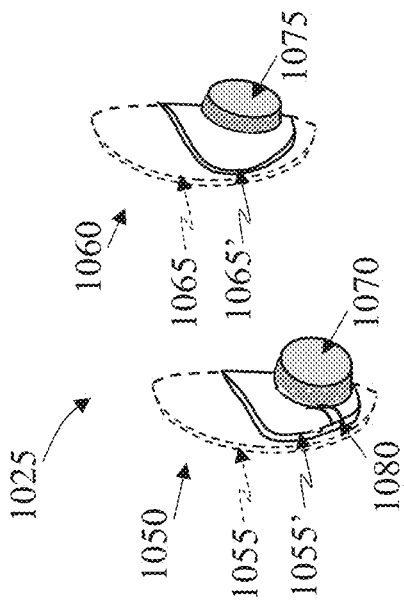
FIG. 8A
FIG. 8B
FIG. 8C

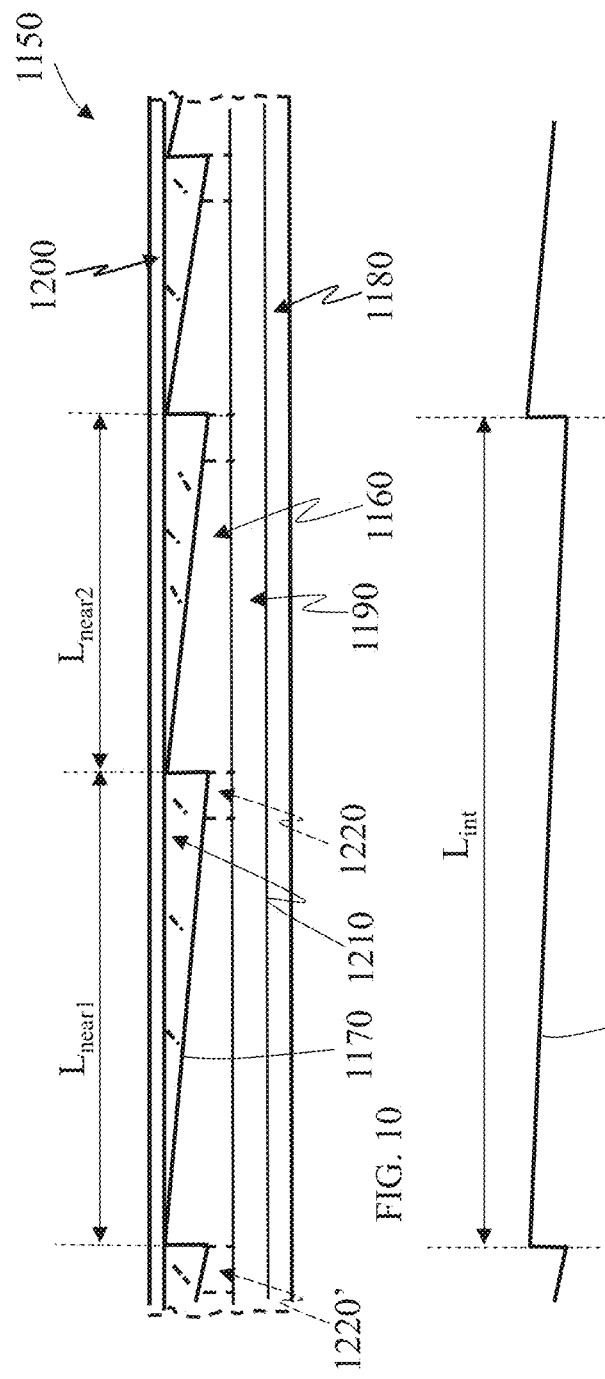
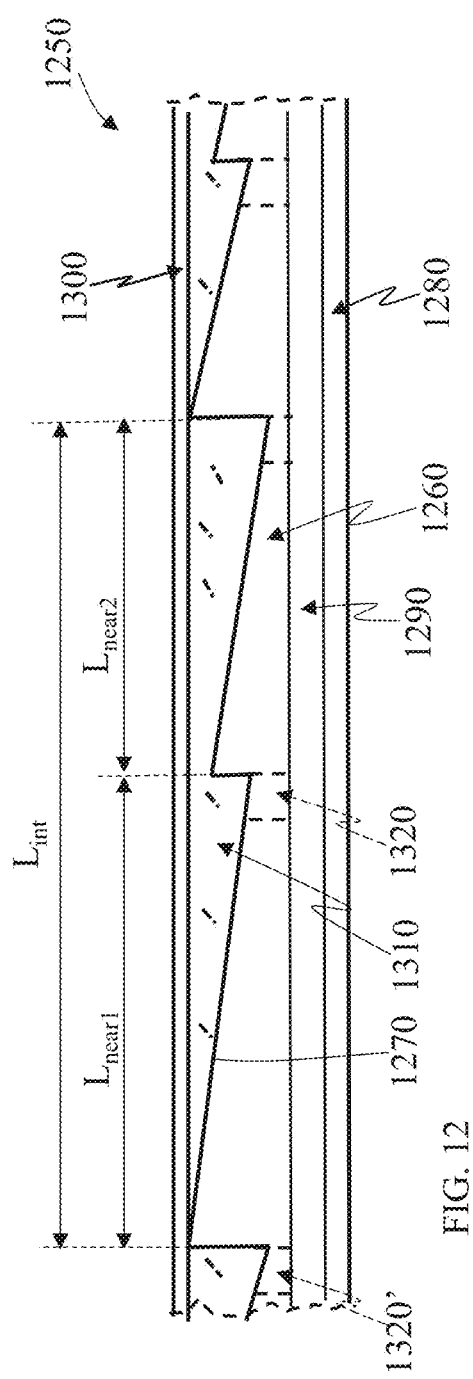

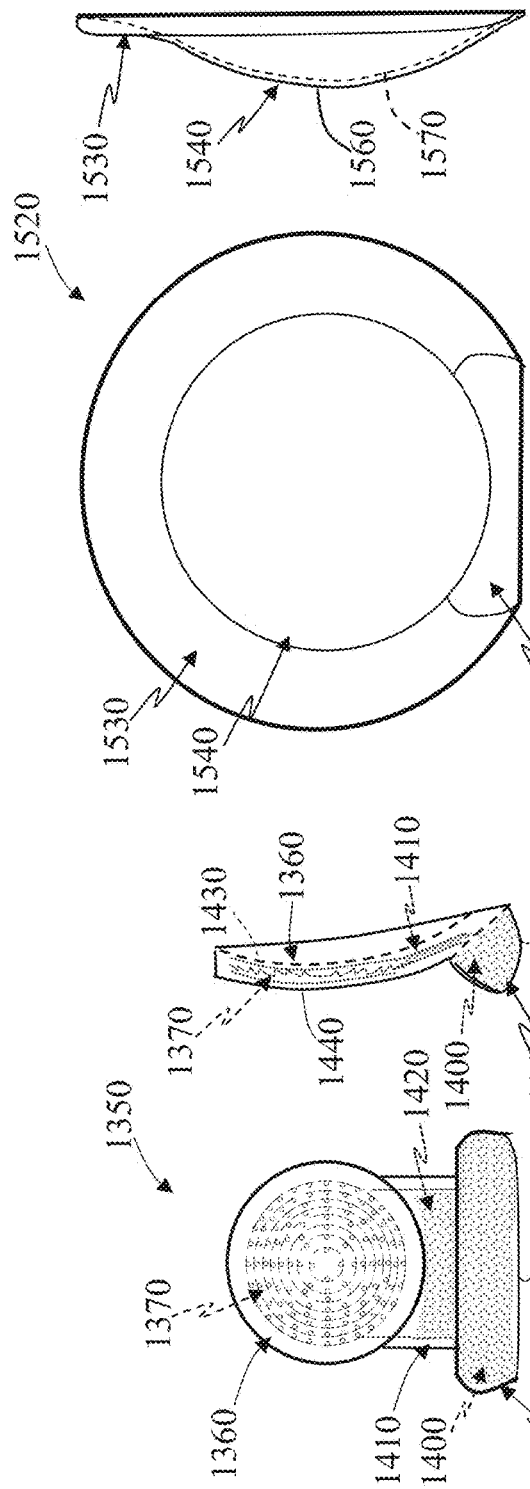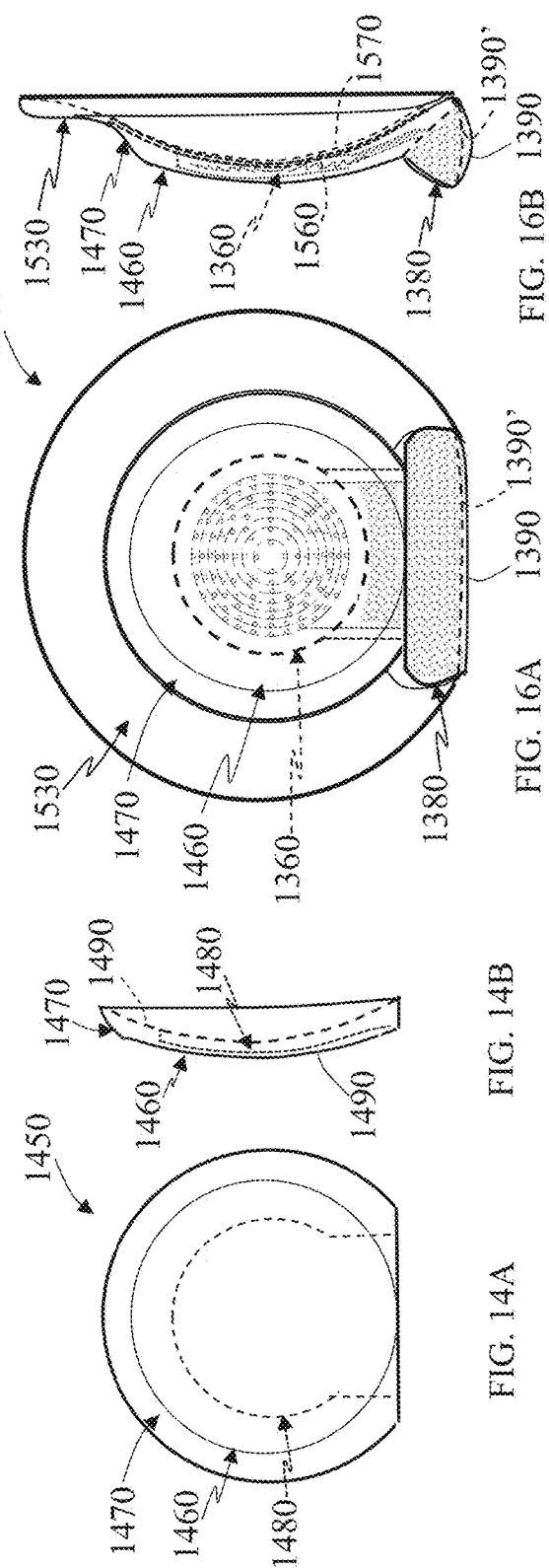

MULTI-CHAMBER SWITCHABLE OPTICAL ELEMENT

CROSS-REFERENCE TO RELATED APPLICATIONS

This Non-Provisional Patent Application claims priority from U.S. Provisional Patent Application Ser. No. 62/970,100 filed Feb. 4, 2020 and the entire content of which is fully incorporated into the present application.

DESCRIPTION

Field of the Invention

The present invention relates generally to a refractive-diffractive switchable lens that creates an image at a position produced by the lens in diffractive state that is different from the image position produced by the lens in refractive state by changing between refractive and diffraction surface shape within the switchable lens, and more particularly to a refractive-diffractive switchable ophthalmic lens that changes image positions by switching between refractive and diffraction surface shapes of far and near foci correspondently for presbyopia correction.

Background of the Invention

U.S. Pat. No. 9,364,319 entitled "Refractive-Diffractive Switchable Optical System" describes switchable cell with matching fluid between a flexible membrane and diffractive guiding surface of the optical substrate, the contents of which are fully incorporated herein with this reference. The corresponding switchable optical device consists of the disclosed optical element that switches between different dioptric powers with the membrane forming refractive surface when the space with the diffractive surface is filled by the matching fluid and diffractive surface when the membrane forms diffractive surface with a periodicity of the diffractive guiding surface when the matching fluid is removed from the space between the membrane and optical substrate.

Ophthalmic lens in the present invention is defined as a diffractive switchable lens suitable for placement outside the eye such as spectacle (eyewear) lens or contact lenses, or inside the eye such as aphakic and phakic intraocular lenses or implants placed in posterior or anterior eye chamber and also included are artificial corneas and corneal implants or inlay. For detailed explanation of the lens of the present invention, the ophthalmic application for presbyopia correction is used as a preferred embodiment.

A space between the elastic membrane and diffractive guiding surface of the optical substrate is very narrow (microns to tens of microns) and consists of periodic segments formed by the shapes of the diffractive grooves of the guiding surface. Thus, an effective removal of the optical fluid from each segment is a challenge and is addressed by the current invention.

Another challenge relates to viscosity of the optical fluid occupying the space between the membrane and diffractive guiding surface as a removal of a fluid with higher viscosity from a narrow space may presents a challenge. Switching between foci by a switchable cell of the U.S. Pat. No. 9,364,319 for presbyopia correction shall be within a fraction of second, and desirably less than 0.5 second. This might be a challenge for an optical fluid of elevated viscosity. A matching fluid to optical substrate materials is likely in the order of 1.45 or higher refractive index and matching fluids with the refractive indices around such values usually manifest a significant viscosity, even 100 times higher than water's viscosity.

Thus, it would be desirable to provide devices and method which address the above deficiencies and weaknesses of the switchable cell described in the U.S. Pat. No. 9,364,319 to provide the means to move the optical fluid from the sections formed in the space between an elastic membrane and diffractive guiding surface and to allow the use of higher viscosity optical fluids.

SUMMARY OF THE INVENTION

The current application discloses the design configuration of switchable optical element with fast fluid transfer for switching between refractive and diffractive states. The switchable optical element is called Surface Based Switchable (SBS) optical element (OE) because switching occurs due to surface shape change between different optical states. Specific configurations of SBS OE and corresponding switchable optical devices for vision, so called Surface Based Switchable (SBS) optical devices (OD), are also disclosed. Definitions of refractive and diffractive states, matching and non-matching fluids, references to materials involved for different elements of switchable optical elements referenced to in the U.S. Pat. No. 9,364,319 are also applied to the current application.

A switchable optical element in accordance with the present invention includes an optical substrate with a diffractive guiding surface forming multiple diffractive grooves and an elastic membrane movable to be in contact with the diffractive guiding surface. In general, the guiding surface might be a refractive surface, but the diffractive surface presents the benefits of a very narrow space between the guiding surface and membrane and all disclosures of the current application will reference to diffractive guiding surface as the preferred embodiment. The diffractive guiding surface can be selected to direct 100% of passing light to a single focus, i.e. kinoform or multimode diffractive surface as described in the U.S. Pat. No. 9,364,319. Such surface is also called relief surface or blazed surface because it manifests saw type of shape where each groove is analogous to a saw tooth. The membrane and optical substrate form an "active chamber" between them filled with an optical fluid. Because a relief consists of periodic diffractive grooves or relief creating repeatable sections of the active chamber that manifests largest and smallest depth within each section over each diffraction groove where the largest depth is at a transition between the sections.

The switchable optical element also includes a substrate cover at the side of the optical substrate opposite of the membrane placement. The substrate and substrate cover form an "internal chamber" that is sized to a dimension of the active chamber. The active chamber and internal chamber are connected by through channels at each and every diffractive groove placed at the deepest part of each active chamber section. If the substrate is made of flat or curved parallel plate, then the thinnest portions of the optical substrate within each groove lies at the deepest portion of the corresponding section of the active chamber, i.e. a channel connects the deepest portion of corresponding active chamber section with the internal chamber. Shapes of the through channels are to match the shapes of the grooves along their thinnest portions. Widths of the through channels may cover several grooves but it is preferably to be a fraction of the groove width to minimize interaction with passing light and effect of membrane. In a simplest form the through channels are circular holes (through holes of any shape). Multiple through channels may be placed at each groove along the deepest portion of the active chamber section and it is desirable that they are equally spaced from each other, for instance, 3 through holes spaced at 120 degrees from each other, or 4 through holes spaced at 90 degrees from each other and so on. The described construction of the switchable optical element is called multi-chamber switchable optical element where two connected chambers (active and internal) with the same optical fluids are at the opposite sides the optical substrate.

Filling the active chamber with an optical fluid, so called "internal fluid", makes a shape of the membrane of certain curvature that includes flat thus creating a first state of switchable optical element. The shape of the membrane surface manifests a certain curvature and is called the refractive surface shape and the corresponding member is in the "refractive form". A second state of the switchable optical element is created when the internal optical fluid is removed from the active chamber into the internal chamber via the through channels. In this second state the elastic membrane conforms to the diffractive guiding surface with the periodicity of the diffractive guiding surface. The shape of membrane surface manifests periodicity of guiding surface and is called the diffractive surface shape and the corresponding membrane is in the "diffractive form". Placing through channels at the deepest portions of the active channel sections allows for almost complete removal of the internal fluid from the active chamber and for the elastic membrane to almost fully conform to a shape of the diffractive guiding surface of the optical substrate by taking the diffractive form. Presence of multiple through channels at each groove along the deepest portion of the section allows for fast fluid movement between the active and internal chambers.

In a preferred embodiment, internal optical fluid is matching fluid to the optical substrate, meaning that its refractive index is equal to or close to the refractive index of the optical substrate material. In this case the through channels are optically invisible and do not produce light scattering. An optical fluid at the opposite side of the elastic membrane is called the "external fluid". It has a different refractive index from the refractive index of the internal fluid. In case of matching fluid being internal fluid, and the active chamber is filled for the membrane to be in the refractive from, such first state of the SBS OE becomes refractive optical state as the matching fluid masks the diffractive guiding surface. The switchable optical element turns into a diffractive second state with the internal fluid being removed from the active chamber into the internal chamber and the membrane taking the diffractive form.

One of the embodiments of the current application discloses self-contained SBS optical element with only one inlet/outlet port connection to the actuation chamber for switching control between the optical states. The disclosed self-contained SBS OE includes membrane cover bonded at the side of the membrane opposite of the substrate. The membrane cover forms an external chamber with the membrane that contains an "external fluid" which is optically different from the internal fluid.

A matching fluid likely manifests a refractive index close to a range of 1.45-1.55 because of a common refractive index of optical substrate materials may run from lower refractive index of acrylic to higher of Ostemer 322, for instance. It is common that fluid viscosity increases with the increase of refractive index making it more challenging to move a more viscous fluid between active and internal chambers via relatively narrow through channels. The option is to have the external fluid to be the matching fluid and to have the internal fluid of lower refractive index and less viscosity for easier transfer between the active and internal chambers. In the case of the external fluid being the matching fluid, the optical states of the switchable optical elements are now in reverse. With the internal optical fluid filling the active chamber for the membrane to take refractive form, the corresponding first state of SBS OE becomes diffractive optical state defined by the diffractive guiding surface. With the internal fluid removal from the active chamber and membrane taking diffractive form, the second state of the SBS OE becomes refractive optical state because the external fluid masks the diffractive guiding surface with the membrane conforming a diffractive guiding surface shape.

To improve membrane conformance, the transitions between the diffractive grooves can be made slated instead of step to allow the membrane to follow the slated groove transitions exactly with the internal fluid removal from the active chamber.

It is also an option not to use a matching fluid either for external or internal optical fluids. In this case, first and second optical states remain in diffractive states, one can manifest single focus performance, say far viewing, and another multifocal performance with split light between intermediate and near foci. This occurs due to the absence of the diffractive guiding surface masking. An optical state with single focus performance may be allocated to far focus as far vision is more demanding, and multifocal performance is allocated to include near focus where it still may provide an acceptable image quality.

Bubbles formation is a common issue with a microfluidic device and a design switchable optical element is to avoid channels and connections with corners, sharp angles or other geometries which are conducive to trapping bubbles.

Another embodiment of the current application includes a disclosure of the diffractive guiding surface (relief) to provide multifocal diffractive state where diffractive relief provides multiple images, for instance for intermediate and near viewing. There are different ways to achieve multifocal diffractive state. For instance, instead of single focus diffractive state to form kinoform or multimode diffractive surface to direct all light to first order diffraction focus, the diffractive grooves height is modified to split the light between first and second orders where the second order is allocated to near and the first order to intermediate viewing.

Another embodiment of the current application is the introduction of a more effective method to create multifocal diffractive state of switchable optical element. It is based on the synchronization method described in the U.S. Pat. No. 8,500,805 by Kobayashi, et al and allows to form several first order diffractive foci for more effective use of light and reduced dependency on a wavelength as compared with the inclusion of a higher order focus, the contents of which are fully incorporated herein with this reference. The synchronization method in the U.S. Pat. No. 8,500,805 describes a process of overlapping of two diffractive reliefs (blaze profiles) at the aphakic lens surface to split light between three or more diffractive foci to produce far, intermediate and near foci. Such reliefs form a synchronous structure where at least two reliefs are set to overlap with each other in a radial direction of the lens to split light between three or more foci. The explanation is that such overlap of reliefs results in the overlap of foci of the reliefs thus allowing to maintain discrete diffractive foci and, therefore, splitting light between several first order foci of each relief. The present application applies synchronization method to diffractive guiding surface of SBS optical element to convert single focus diffractive state into multifocal diffractive state. The description is provided for the condition when the SBS OE single focus refractive state is allocated to far viewing which is more practical as far viewing is more demanding. Conceptually, multifocal diffractive state may be also allocated to far viewing.

The application of synchronization method to switchable optical element has been described in the example of surface-based switching but it can also be applied to electro-active switchable element described in the U.S. Pat. No. 6,857,741 by Blum R D, et al., U.S. Pat. No. 8,523,354 by Haddock J N, et al. and others, this is so called material-based switching (MBS), the contents of which these applications are fully incorporated herein with these references. An electro-active material such as liquid crystal, for instance, is contained by the surface relief diffractive structure at the surface or in a form of volume diffractive structure, and the synchronization method is applied to the corresponding material based switching optical element to create multifocal performance in its diffractive state.

Add power for presbyopia correction usually goes up to about 3.0 D (at spectacle plane) but the design of guiding surface of switchable optical element may provide higher Add power to apply magnification which is desirable for low vision patients with compromised retina. Commonly used magnification is 2×-4× which corresponds to about 5 D-10 D of Add power. Magnification application can be used in IOL application as well as in contact lens and eyewear (spectacles) applications where the subject can control switching to the magnification state manually or touching in case of eyewear or by lower eyelid in case of contact lens. The design of the SBS optical element is maintained regardless of the Add power except for the guiding surface where the periodicity controls Add power.

Another embodiment of the current application includes a disclosure of 3-state switchable optical element. The SBS OE includes two optical substrates with their diffractive guiding surfaces facing each other and an elastic membrane placed in between thus creating two active chambers. The membrane now can be in three states: (1) one diffractive form when conforming to one of the diffractive guiding surfaces; (2) refractive form when the optical fluids fill both active chambers; and (3) another diffractive form when conforming to another diffractive guiding surface. 3-state switching allows for switching between near, intermediate and far foci by a single 3-state SBS OE. The structure includes multi-chamber construction with each optical substrate having own internal chamber from by substrate covers at the opposite side of the membrane with through channels connecting active chambers with corresponding internal chambers.

Multifocal diffractive state of a switchable optical element opens the opportunity for a magnifying state in addition to the far and near states of the SBS OE. For instance, contact lens or glasses with normal far and near foci, say near focus at 3 D Add power, i.e. normal reading distance of 33 cm, may also include 6 D Add to provide magnification due to short viewing distance of about 17 cm, i.e. equivalent to 1.5×magnifier. If applying different synchronization, the magnifying add power can be 9 D, i.e. the viewing distance is about 11 mm which is equivalent to 2.25×magnifier.

Another embodiment of the current application is to use multi-chamber SBS OE to remotely neutralize a multifocal performance of multifocal IOL. The multifocal IOL optical body is embedded with a multi-chamber switchable optical element with a diffractive guiding surface being a multifocal guiding surface of a selected multifocal design. One of the external or internal chambers of the optical element is connected to so called single-usage actuator that includes flexible and deformed diaphragm separating holding chamber connected to one of the external or internal chamber. The diaphragm separates holding chamber and stopper chamber filled with a gas and having a stopper inside it to maintain the diaphragm in a deformed state of the elevated strain. The stopper is made of a flowable material that can be melted by a laser beam. Upon melting the stopper, the flexible diaphragm takes the undeformed state of lower strain and pushes or pulls fluid in or out of the holding chamber which consecutively, pushes the fluid out or in of external or internal chamber. The process changes the state of the switchable optical element from multifocal to monofocal state by masking multifocal guising surface. Using another single-use-actuator for pulling or pushing the fluid, the process can be received to convert monofocal state into the multifocal state defined by the multifocal guiding surface of the substrate.

The disclosed multi-chamber switchable optical element also has an advantage for transferring single focus lens of an eyewear into presbyopia correcting lens at the same spectacle frame. The method of conversion has a great advantage of spectacle frame independence thus allowing a wearer to choose any preferred spectacle frame, generically called a base member. The method includes a placement of switchable element acting as the "active member" of so-called "convergent system" at the back of the eyewear lens (it can be at the front as well) of the single focus original lens which is a "refraction member" because it provides refraction correction. Back placement has an advantage in that the back surface of a single focus lens usually serves as a base surface of the eyewear lens and manifests a limited set of curvatures. The convergent system includes all elements for presbyopia correction-switchable optical element as the active member, actuator connected to active member by a channel and a control member. Upon assembly of single focus lens (refraction member) and convergent system, all these elements are maintained within the lens itself providing spectacle frame independence. The control member may include a simple manual control or electronic control. The convergent system can be applied to either surface based switching or material based switching via electroactive materials and also for adjustable or variable active member to form fluidic lens or Alvarez lens.

The disclosed multi-chamber switchable optical element also has an advantage for transferring a single focus contact lens into a presbyopia correcting lens while maintaining optimum fitting. The method is analogous to the one disclosed above for eyewear lens. The method also includes a placement of switchable element as active member of the convergent system at the back of the refraction member serving for refraction correction. The convergent system also includes all elements for presbyopia correction-switchable optical element as the active member, actuator connected to active member by a channel and a control member. Upon assembly of a single focus unit (refraction member) and convergent system, this assembly is combined with a base member which includes a contact lens lenticular used for an optimum contact lens fitting over the eye. The control member may include a simple manual control or electronic control. The convergent system can also be applied to either surface based switching or material based switching via electroactive materials and also an adjustable fluidic (balloon type) active member.

Features and advantages of the present invention will become apparent from the following more detailed description, when taken in conjunction with the accompanying drawings, which illustrate, by way of example, the principles of the invention.

BRIEF DESCRIPTION OF THE DRAWINGS

The advantages and features of the present invention will be better understood by the following description when considered in conjunction with the accompanying drawings in which:

FIG. 1, FIG. 2 and FIG. 3 describe a section of a multi-chamber SBS optical element in two optical states with through channels at the diffractive grooves of the optical substrate at the deepest portions of the active chamber sections;

FIG. 4A and FIG. 4B demonstrate a front view and cross-section view of the multi-chamber SBS optical element in the configuration where the internal chamber is connected to an actuation chamber;

FIG. 5A and FIG. 5B demonstrate a front view and cross-section view of the multi-chamber SBS optical element in the configuration where the external chamber is connected to an actuation chamber;

FIG. 7A and FIG. 7B show a front view and a cross-section view of a multifocal IOL with multi-chamber SBS optical element operated by a single-use actuator for deactivating multifocal state or reactivating multifocal state;

FIG. 8A through FIG. 8C show the assembly method of a manually actuated Eyewear lens for switching between foci with the use of switchable multi-chamber optical element as an active member;

FIG. 10, FIG. 11 and FIG. 12 demonstrate a conversion of single focus diffractive guiding surface into bi-focal diffractive guiding surface by synchronization method shown within a section of the multi-chamber SBS optical element with the membrane in refractive form; and FIG. 13A through FIG. 16B show the assembly method of manually actuated contact lens for switching between foci with the use of multi-chamber optical element as an active member.

DETAILED DESCRIPTION OF THE PREFERRED EMBODIMENTS

Figure 6:
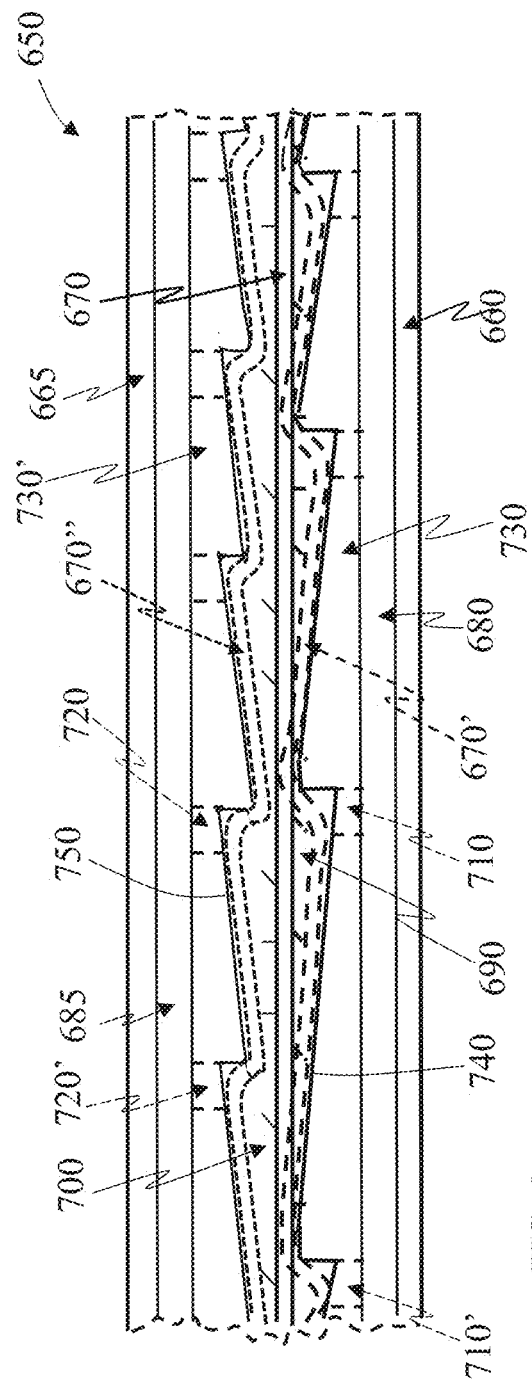
FIG. 6 shows a cross-section of a 3-state multi-chamber SBS optical element.

FIG. 1 shows a simplest shape of SBS OE as a circular disc with a rectangular cross-section. A cross-section can also be meniscus, plano-convex, plano-concave or other shapes. The optical axis 100 and segment 110 or 110' of switchable optical element are referenced to in the FIG. 1. The dimensions of a switchable ocular element might vary significantly between different applications, from about 4 mm diameter in intraocular and contact lens application to about 30 mm diameter in eyewear lens application. The thickness may be about 100 microns or less to meet such challenging application as contact lens or corneal implant.

FIG. 2 demonstrates the segment 110 cross-section of a preferred embodiment of a switchable optical element with elastic membrane 140 being in refractive form, flat in this case but it can also be curved. The switchable optical element of the present embodiment includes active chamber 150 between the elastic membrane 140 and diffractive guiding surface 190 of the optical substrate 160 filled with an internal fluid 151, 151'. The internal fluid may be a matching fluid to the optical substrate, i.e. its refractive index being equal to or close to the refractive index of the optical substrate material; or be a non-matching fluid meaning its refractive index is substantially different from a refractive index of the optical substrate 160. An internal chamber 180 is formed between the optical substrate 160 and substrate cover 165, where the internal chamber is disposed on an opposite side of the optical substrate from the active chamber. The active chamber 150 is connected with the internal chamber 180 via a plurality of through channels 170, 170' and so on, optimally placed at the deepest portion of the active chamber 150 at each diffractive groove of the guiding surface. The deepest portion is in regards to the deepest depth of the active chamber 150, which in this case coincides with the thinnest portion of the optical substrate 160 at each groove because of its plano-parallel cross-sectional shape. In simplest forms the through channels are through holes, which can be circular, oval, rectangular or any other suitable shape.

In the case of the matching fluid occupying the active chamber 150, transitions between the grooves may be of typical step shape of blazed surface because a guiding surface shape is masked by the matching optical fluid. The matching fluid also masks the through channels 170, 170' and so on, thus avoiding light scattering at the through channels. In case of non-matching fluid occupying the active chamber 150, it is desirable to have slanted transitions between the grooves as shown by the shape 220 at one of the grooves. Slanting the transition between the grooves slightly reduces groove width from L to L' as shown at one groove but helps with more complete removal of the optical fluid from the active chamber 150 which is beneficial in case of non-matching optical fluid. It is desirable also to truncate slightly the groove peaks as shown by 240 at one of the peaks and round them up as shown by 230 at one of the peaks of the diffractive grooves in order to minimize any damage to the elastic membrane 140 and reduce strain of the elastic membrane when stretching for conforming to the diffractive guiding surface shape.

A self-contained switchable optical element includes a membrane cover 120. The membrane cover forms external chamber 130 with the membrane 140 which may be of a very shallow depth. The membrane may even reach surface 210 with filling of the active chamber which offers more control for with fluid transfer in and out of the active chamber due to limiting a shape variation of the membrane. The external chamber 130 is filled with non-matching fluid if matching fluid used in the internal chamber 180, or matching fluid if non-matching fluid is used in the internal chamber 180. The FIG. 2 shows the membrane 140 at a minimum strain in refractive form. With matching fluid occupying the active chamber 150, the switchable optical element on FIG. 2 is in the refractive state. If non-matching fluid occupying active chamber 150, the switchable optical element on FIG. 2 is in diffractive state. In general, elastic membrane can also be in a radially stretched out for controlling its elastic characteristics and thus effecting so called "trigger pressure" required to change its shape between refractive and diffractive forms.

Surface 210 may include additional optical characteristics such as asphericity or bi-asphericity to improve lens performance such as IOL, for instance. Surface 190 may also include additional optical characteristics such as extended depth of focus (EDOF) at near to provide intermediate foci. For instance, EDOF of diffractive design would include very low add multifocality to direct some fraction of light from $1^{st}$ order of diffraction allocated to Near focus to $2^{nd}$ order for intermediate distance (≈0.5 meter to ≈2 meters).

FIG. 3 demonstrates a cross-section of segment 110' of preferred embodiment of a switchable optical element with membrane 140' being in state of conformance to a shape of the diffractive guiding surface 190 of the optical substrate 160 as shown by the membrane surface 250, i.e. the membrane is taking diffractive form. The optical fluid is removed from the active chamber into internal chamber 180 using through holes 170, 170' and so on. Slated shape of the transitions between the grooves helps to remove all fluid from the active chamber as shown by the equivalency between membrane transition 260 and transition 220 of the guiding surface 190. A different optical fluid occupies the external chamber 130' between membrane 140' and membrane cover 120. If a matching fluid occupies the active chamber, then the FIG. 3 would demonstrate switchable optical element in the diffractive optical state as the membrane 140' is in diffractive form with diffractive surface 250 equivalent to the diffractive guiding surface 190. If a non-matching fluid occupies the active chamber, then the FIG. 3 would demonstrate switchable optical element in the refractive optical state as the membrane 140' is in diffractive form with diffractive surface 250 shape is equivalent to the shape of the diffractive guiding surface 190.

FIG. 4A demonstrates a front view of SBS optical element 300 of specific construction with multiple small holes 410, 410', 410" and so on, through the optical substrate 340 at the diffractive grooves 420, 420' 420" and so on. These are through channels which can be located spaced apart along an arch shape along the groove shape. Diameters of the holes are largely defined by the membrane thickness to minimize a deformation of the membrane within the holes and diffractive groove widths. They might be about 30-50 microns diameter in IOL and contact lens applications where the groove width is about 100 microns, to about 0.3 mm diameter in eyewear (spectacle) lens applications where the groove width is about 0.8 mm. Small holes can be produced by a laser drilling and larger holes can be fabricated by mechanical micro-drilling or the like. As shown herein, the number of holes are about hundred and they are spread out at each diffractive groove at the thinnest part of substrate within each groove. The holes locations on FIG. 4A is at the external edge of each groove which is common for a positive power blazed type diffractive surface. As an example, the FIG. 4A references to the locations of holes at $1^{st}$, $3^{rd}$ and $6^{th}$ grooves. The holes are placed at the internal edge of each groove in case of a negative power blazed type diffractive surface where the thinnest parts of the substrate at each groove would be located.

Switchable optical element 300 includes a substrate cover that creates an internal chamber 350 with the substrate 340. An elastic membrane is located at the diffractive grooves at the side of the substrate 340 opposite to the internal chamber 350 to form active chamber with the substrate 340. The active and internal chambers are filled with an optical fluid. Actuator connector 405 is attached to the substrate cover. And the internal chamber 350 is connected by the channel 355 inside the actuator connector 405 and having inlet/outlet port 400 at the external end. The actuator connector 405 is connected to an actuation chamber that controls a fluid transfer in and out of the internal chamber 350 and in turn, the active chamber. The substrate cover maintains post 370 at the center of the optical element 300 to support thin substrate 340 shape during the internal fluid transfers. If the fluid is pulled out through the port 400, the fluid is removed from the active chamber through the channels 410, 410', 410" and so on for the membrane to conform to the shape of the diffractive guiding surface of the substrate 340. Such configuration of the switchable optical element with the actuator connected port at the internal chamber is called "pull-out for conformance" design. The FIG. 4A also includes membrane cover 310 bonded with the membrane or other parts of the switchable optical element and forming external chamber 320 with the membrane 330 of the substrate cover. The substrate cover also forms accumulator pocket 380 with the membrane 330. Its function will be explained below with the demonstration of a cross-sectional view of the switchable optical element 300.

FIG. 4B shows a cross-sectional view of the optical element 300. It includes substrate support 360 and optical substrate 340 attached to the substrate support at the periphery and supported or attached at its center by the post 370 of the substrate support 360. Substrate support 360 and optical substrate 340 form internal chamber 350 filled with optical fluid. An actuator connector 405 is attached to the substrate support 360 with a connector channel 355 connecting the internal chamber 350 at one end and inlet/outlet port 400 for connection to an actuation chamber at the other end. The optical element 300 includes elastic membrane 330 in close proximity to the diffractive guiding surface of the optical substrate 340 forming active chamber in between. Active chamber and internal chamber 350 are connected by multiple through channels through the optical substrate 340 at each diffractive groove where one of the channels 410 is shown at $6^{th}$ groove. Membrane cover 310 is bonded to membrane 330 or substrate cover at the opposite side from the optical substrate 340 to form external chamber 320 filled with a different optical fluid. One of the optical fluids, preferably fluid in active and internal chambers is matching fluid to the optical substrate 340.

There is also accumulator pocket 380 within the substrate support 360 communicating with the membrane 330 at the side opposite to the external chamber 320. It is filled with gas to assist in maintaining external fluid volume of the external chamber with the internal fluid transfer in and out of the active chamber which results in membrane shape change between refractive and diffractive forms. FIG. 4B shows the membrane 330 in refractive form, flat shape in this case though it can be curve shape. If an amount of internal fluid is removed from the internal chamber via port 400, the fluid is transferred from the active chamber with membrane conforming to the guiding surface thus creating an additional space in the external chamber. As the fluid in the external chamber is not expandable, it must come from somewhere to take the vacated space of the active chamber. This is when the accumulator pocket comes into play—due to gas-filled nature of the accumulator pocket, the membrane within the pocket 380 bulges towards the accumulator pocket 380 taking the volume equals to the space vacated by the active chamber. As the internal fluid from the actuation chamber is transferred back to the internal chamber to bring the membrane into refractive form of non-conforming state, the membrane takes some volume of the external chamber equivalent to the active chamber. As a result, the membrane at the accumulator pocket takes a shape that reduces the accumulator pocket volume by the space taken by the actuator chamber. Thus, the accumulator pocket allows to fully enclose the external chamber 320 and leave only one port 400 at the internal chamber 350 for communication with the actuation chamber.

In terms of assembly for the SBS optical element 300, the membrane cover 310 and substrate support 360 would each consists of two parts—ring shape and central plug. Both ring shape parts hold together membrane 330 and substrate support 340 by their internal areas and are adhered together at their external areas thus exposing the most of membrane and optical substrate for a corresponding fluid filling. The active chamber between membrane 330 and substrate 340 are filled with the fluid as well as the exterior of the substrate 340 within the ring portion of the substrate cover with the channels through the substrate 340. The plug part of the substrate support 360 is adhered to the internal area of the ring part of the substrate support 360 to form the internal chamber 350 with an excess of the fluid removed. Similarly, inside of ring part of the membrane cover 310 is filled with another fluid and then the plug part of the membrane cover 310 is adhered to the internal area of the ring part of the membrane cover 310 to form external chamber 320 with an excess of the fluid removed. The SBS optical element 500 can be assembled by a similar process.

FIG. 5A demonstrates a front view of the SBS optical element 500 of specific construction with multiple small holes 610, 610', 610" and so on through the optical substrate 540 at the diffractive grooves analogous to one described in FIG. 4A. There is external chamber 550 between the membrane cover 510 and membrane. The external chamber 550 is connected to the channel 590 inside the actuator connector 605 with an inlet/outlet port 600 at the external end. The actuator connector 605 is connected to an actuation chamber that controls a fluid transfer in and out of the external chamber 550. Optical element 500 includes a substrate cover that creates an internal chamber 520 with the substrate 540. The substrate cover maintains post 570 at the center of the optical element 500 to support the substrate 540 to maintain its shape during external fluid transfers. An elastic membrane is located at the diffractive grooves at the side of the substrate 540 opposite to the internal chamber 520 to form active chamber with the substrate 540. The active and internal chambers are filled with an internal fluid. If the external fluid is pushed into the external chamber 550 through the port 600, the membrane is pushed in against the diffractive guiding surface and the internal fluid is removed from the active chamber through the channels 610, 610', 610" and so on, into the internal chamber. The membrane conforms to a shape of the diffractive guiding surface of the substrate 540 by taking guiding surface periodicity of the grooves and grooves height. Such configuration of the switchable optical element with the actuator connected port at the external chamber is called "push-in for conformance" design. The membrane cover 510 also forms accumulator pocket 580 with the membrane. Its function is equivalent to the one explained in FIG. 4B and some details will be added when demonstrating a cross-sectional view of the switchable optical element 500.

The optical element 500 as well as 300 of FIG. 4A are microfluidic devices and filling their chambers with fluids without bubbles might be a challenge. FIG. 5A demonstrates the ports for filling the external, internal and active chambers with the corresponding external and internal fluids. Similar description would be applied to FIG. 4A. Each chamber includes 2 connectors with corresponding channels/ports for filling up with the corresponding fluids via one connector and removing air/gas via other connector. The external chamber 550 includes connector 555 with a channel inside and port 555'. The connector 550 may clamped or adhered to the membrane cover 510 like one of the actuator connector 605. The internal chamber 520 includes connector 640 with port 645 and opposite connector 640' with port 645'. The connectors 640 and 640' are clamped or adhered to the substrate support. The active chamber also includes connector 630 with the channel inside and opening 620 at the active chamber with port 635, and opposite connector 630' with a channel inside and opening 620' at the active chamber with port 635'. The connectors 630 and 630' might also be clamped or adhered to the substrate support. Upon filling the external, internal and active chambers, all ports are sealed accept the actuator port 600 connected to the actuation chamber. The overall connections are such that to avoid sharp corners when placing channels between the ports and corresponding chambers as well as external connections. Hydrophobic materials, such as PDMS, tend to be source of Harvey nuclei. A treatment with oxygen plasma increases the hydrophilicity for a certain period of time to run the assembly or of the material at the surface with hydrophilic groups can be applied. Another possibility is to fill the chambers in the vacuum.

FIG. 5B shows a cross-sectional view of the switchable optical element 500. It includes substrate support 560 and optical substrate 540 attached to the substrate support at the periphery and supported or attached at its center to the post 570 of the substrate support 560. Substrate support 560 and optical substrate 540 form internal chamber 520 filled with an internal fluid. Membrane cover 510 is bonded with the membrane 530 or substrate cover to form external chamber 550 in between which is filled with an external fluid. An actuator connector 605 is attached to the membrane cover 510 with a connector channel 590 connected the external chamber 550 at one end and having inlet/outlet port 600 for connection to an actuation chamber at the other end. The optical element 500 includes elastic membrane 530 in a close proximity to the diffractive guiding surface of the optical substrate 540 forming active chamber in between. Active chamber and internal chamber 520 are connected by multiple through channels through the optical substrate 540 at each diffractive groove where one of the channels 610 is shown at $6^{th}$ groove.

There is also accumulator pocket 580 within the membrane cover 510 communicating with the membrane 530 at the side opposite from the internal chamber 520. It is filled with gas and serves to maintain volume of the internal fluid with membrane shape change between refractive and diffractive forms. FIG. 5B shows the membrane 530 in refractive form of flat shape. If some amount of external fluid is injected into the external chamber 550 via port 600, the membrane 530 is pushed against the diffractive guiding surface thus pushing the internal fluid out of the active chamber into the internal chamber 530. The membrane 530 bulges into the accumulator pocket 580 by the same volume of internal fluid that is pushed out of the active chamber. As the same amount of optical fluid is removed from the external chamber 550 through port 600, the membrane takes refractive form as the same fluid volume is transferred from the internal chamber 510 into the active chamber. The membrane at the accumulator packet 580 takes then the original shape taking the accumulator volume equivalent of the active chamber volume taking by the internal fluid. Thus, the accumulator pocket allows to enclose the internal chamber 520 and to leave only one port 600 at the external chamber 550 for communication with an actuation chamber.

FIG. 6 shows a section of 3-state multi-chamber SBS optical element 650. It includes two optical substrates 730 and 730'. The optical substrate 730 includes diffractive guiding surface 740 and optical substrate 730' includes diffractive guiding surface 750. In general, it might be a refractive surface. There is elastic membrane 670 placed between the guiding surfaces 740 and 750 separating active chamber 690 and active chamber 700 each filled with different optical fluids. Membrane 670 is shown in refractive form. This is state 1 where the optical element 650 manifests one dioptric power value. It is desirable to have the membrane 670 in a close proximity to both guiding surfaces 740 and 750 to minimize the amounts of the optical fluids to be transferred in the active chambers 690 and 700. The optical element 650 also includes substrate support 660 and substrate support 665 to form internal chamber 680 between substrate 730 and substrate support 660 and internal chamber 685 between substrate 730' and substrate support 665. The internal chamber 680 is connected with active chamber 690 by through channels 710, 710' and so on at each diffraction grooves of the guiding surface 740. The internal chamber 685 is connected with active chamber 700 by through channels 710, 720' and so on at each diffraction grooves of the guiding surface 750.

By moving optical fluids in and out of an active chamber allows to conform the membrane 670 to two different guiding surfaces and create two additional power values of the optical substrate 650 in addition to an optical power with the membrane in the refractive form. For instance, the membrane takes shape 670' with the optical fluid as it moves out of the active chamber 690 into internal chamber 680 via through channels 710, 710' and so on and another optical fluid of active chamber 700 fills the released space by transporting the corresponding optical fluid from the internal chamber 685 into the active chamber 700 via through channels 720, 720' and so on. The membrane would take shape 670" with the optical fluid at it moves into of the active chamber 690 from internal chamber 680 via through channels 710, 710' and so on and optical fluid of active chamber 700 is moved out from active chamber 700 into the internal chamber 685 via through channels 720, 720' and so on.

Several options of 3-state performance are possible. In a first embodiment the substrates 730 and 730' are made of different material of different refractive indices where the optical fluid of active chamber 690 is a matching fluid for substrate 730 and optical fluid in active chamber 700 is a matching fluid for substrate 730'. The optical element 650 with membrane in flat shape 670 would provide refractive power because each optical fluid masks the corresponding diffractive guiding surface. The optical element 650 comes into one diffractive power defined by the guiding surface 740 with membrane conforming shape 670' and another diffractive power is defined by the guiding surface 750 with membrane conforming shape 670'. Thus, the optical element 650 manifests three levels of optical powers, one refractive power and two diffractive powers for tri-state switchable optical element.

In another embodiment the optical substrates 730 and 730' are made of the same material with the fluid in active chamber 690 that is the matching fluid for the substrates and fluid in active chamber 700 is a non-matching fluid. The optical element 650 is in a diffractive state with power controlled by the guiding surface 750 when the membrane manifests shape 670. Optical element 650 is in a different diffractive state with the power defined by a sum of powers produced by guiding surfaces 740 and 750 when the membrane manifests shape 770'. The optical element 650 is in the refractive state as the space between guiding surface 740 and 750 is filled with matching fluid when the membrane manifests shape 670". Another embodiment includes optical element 650 with both non-matching optical fluids. In this case all three power levels are of three different diffractive powers.

Another option of 3-state multi-chamber SBS involves a modification of the 3-state multi-chamber SBS optical element 650 by adding another membrane next to 730' where the membrane 670 is placed next to the substrate 730. One membrane then manifests a more rigid elastic characteristic, for example, it may be thicker than the other membrane. Different fluids might be placed between a membrane and the corresponding optical substrate, but for the explanation purpose, matching fluid to the corresponding optical substrate is placed between the corresponding membrane and optical substrate, i.e. the corresponding active chambers. As a different fluid is injected between the membrane, say, a non-matching fluid, the more elastic membrane takes a diffractive form by conforming to the corresponding guiding diffractive surface of the optical substrate first. The other membrane still maintains refractive form with the fluid filling the corresponding active chamber. The SNS optical element is now transferred into first diffractive state of a certain optical power. As more non-matching fluid is transported between the membranes, the second membrane conforms to the guiding diffractive surface of the corresponding optical substrate transferring the SNS optical element into another diffractive state of third optical power.

The described above the 3-state SBS structure with two membranes may help the application of SBS optical element to a low vision aid that involves switching between large power differences where one power, say diffractive power, manifests high optical power. To create high diffractive power would require a significant increase in a number of grooves thus resulting in very narrow diffractive grooves of corresponding guiding diffractive surface of an optical substrate which is difficult to produce and also the through channels within the groove may be of too small a size for effective fluid transfer in and out of the active chamber. In this case, 3-state multi-chamber SBS optical element with two membrane can be modified into 2-state SBS optical element with equivalent for elasticity membranes and where each guiding surface responding for half of a high power switching. Assuming again as an example, a matching fluid filled the active chambers between membrane and corresponding optical substrate and a non-matching fluid is injected between the membrane. As the membranes have an equivalent elastic property, they both conform to the corresponding guiding diffractive surfaces with non-matching fluid injection between the membranes. The high power switching now is produced by the sum of each diffractive surfaces of the optical substrates. The benefit is that each guiding diffractive surface now would require twice wider diffractive grooves.

FIG. 7A demonstrates a front view of switchable multi-focal IOL (SMIOL) 800. The optical body 940 of the SMIOL 800 includes switchable optical element 810. It is the same construction as described by FIG. 4A through 5B with one exception—the diffractive guiding surface is a multifocal diffractive design instead of monofocal diffractive design, i.e. the light passing through multifocal diffractive guiding surface splits into multiple foci. In general, a guiding surface of the element 810 might be a refractive multifocal surface. The optical body 940 also includes actuator member 820 and actuator member 830. They are single-usage actuators and both are in loaded states. They both have similar constructions but exert opposite actions, as actuator 820 is to neutralize multifocal performance of the optical element 800 for monofocal performance and actuator 830 is to convert monofocal performance back to the multifocal performance.

The actuator 820 includes flexible deformed diaphragm 870 separating stopper chamber 850 and holding chamber 840. The diaphragm 807 is made of a flexible material such as metal or plastic which can stay in an elevated strain state when deformed under a load and returns into a minimum strain state when the load is removed. Stopper chamber 850 is filled with gas and holding chamber 840 is filled with internal fluid of the optical element 810 if connected to the internal chamber of the switchable optical element 810. A configuration may connect a single-usage actuator equivalent to 820 and 830 with the external chamber also that external fluid fills a holding chamber. Assume that single-usage actuator 820 (and 830) is filled with a matching fluid of the internal chamber of the optical element 810 of the configuration similar to one described on the FIGS. 4A and 4B and is connected with the internal chamber by the channel 880. The diaphragm 870 is maintained in deformed state by stopper 860 placed inside the stopper chamber 850 and is made of a flowable material such a thermoplastic, for instance. As the stopper 860 irradiated by a laser beam, it melts and load on the diaphragm 870 is removed to allow the diaphragm to take shape 870' of a minimum strain. The volume of stopper chamber 850 increases and holding chamber 840 reduces with the diaphragm 870 pushing the matching fluid into the internal chamber of the optical element 810. The matching fluid in turn fills the active chamber connected with internal chamber by through channels. The membrane of the optical element 810 goes from the conformed state to the multifocal guiding surface to un-conformed state of refractive form with matching fluid masking the multifocal guiding surface thus neutralizing a multifocal performance of switchable SMIOL 800. The actuator construction might be such that the diaphragm takes a shape that reduces a volume of the stopper chamber with stopper irradiating. This would increase a volume of holding chamber connected with the external chamber, for instance, to pull out a non-matching fluid from the external chamber of optical element as described by FIGS. 5A and 5B which also masks the multifocal guiding surface by the matching fluid to neutralize SMIOL multifocal performance.

The construction of actuator 530 is equivalent to the construction of actuator 820. It also includes flexible diaphragm 920 in deformed state separating stopper chamber 900 and holding chamber 890 connected with internal chamber of the optical element 810 by channel 930. A deformed state of the diaphragm 920 is maintained by the stopper 910 also placed inside the stopper chamber 900. Upon laser beam irradiation, the flowable material of the stopper 910 melts releasing the diaphragm 920 into its undeformed shape 920'. This, in turn pulls matching fluid from the internal chamber of optical element 810 into holding chamber 890 thus forcing the membrane of the optical element 810 to conform to the multifocal guiding surface converting SMIOL 800 from monofocal performance back to the multifocal one. The design of single-usage actuators may be to push or pull the matching fluid or un-matching fluid for converting the switchable optical element between multifocal and monofocal performances.

FIG. 7B shows a cross-section of the SMIOL 800 analogous to one shown on FIG. 4B with internal chamber 990 of the optical element 810 being connected to the holding chamber 840 of the actuator 820 by channel 880. The membrane 980 of the optical element 810 conforms to the multifocal guiding surface of the optical substrate 970 to manifest multifocal performance by the SMIOL 800. Non-matching fluid occupies the external chamber 1000. The load state of the actuator diaphragm 870 is maintained by the stopper 860 inside the stopper chamber 850 which is filled with gas. The optical element 810 is encapsulated by optical body 940 with front optical surface 950 and back optical surface 960 to provide far focus of the SMIOL 800.

FIG. 8A, FIG. 8B and FIG. 8C describe a method of conversion of a single focus Eyewear into adjustable power Eyewear between at least two different foci, for instance, far and near foci or far and intermediate foci. This is called "Multi Viewing Conversion" abbreviated as MVC. For this application, far distance is defined as 2 meters (about 6.5 feet) from the eye and beyond, near distance is defined as 0.5 meter (1.64 feet) from the eye and closer and intermediate distance is defined as the distance between 0.5 meter (1.64 feet) and 2 meters (about 6.5 feet). The optical power adjustable or switchable Eyewear can be analog type where optical power changes continually from one focus to another or digital type where optical power switches between foci. A mechanism of power adjustment or switching might be (a) fluidic based where lens changes its shape with fluid volume change inside the lens, (b) Alvarez type design where fluidic chamber or electro-mechanical actuator pushes one of the wave plates in respect to another to adjust for optical power, (c) switching between surface shapes as described in FIG. 4A through FIG. 5B which is called "surface based switching" abbreviated as SBS or (d) material based switching by "electro-active material" abbreviated as MBS.

The preferred embodiment is to conduct multi viewing conversion by the SBS OE for quick switching between foci where SBS OE is a multi-chamber construction described by FIGS. 4A and 4B or FIGS. 5A and 5B, but it is fully applicable to any other mechanism of optical power adjustable or switchable Eyewear. The MVC to be demonstrated with the use of multi-chamber SBS optical element.

FIG. 8A shows single focus Eyewear 1010 consisting of frame 1020, right single focus lens 1030 and left single focus lens 1040. Lenses 1030 and 1040 may include sphero-cylinder corrections. A single focus lens is called refraction member of the Eyewear because it provides refraction correction.

FIG. 8B shows "Conversion System" 1025 abbreviated as CS consisting of "right CS" 1050 to be used for MVC of right lens 1030 and "left CS" 1060 to be used for MVC of left lens 1040. Right CS consists of "right carrier" 1055 which is described as a thin sheet made of an eyewear material or preferably an elastic material such as silicone type, for instance. It can be of a rounded shape of about 50 mm diameter equivalent to the diameter of an eyewear lens blank. An SBS optical element acting as active member is embedded at the front side of the carrier 1055. It is connected to an actuator by tubing and the actuator is connected to a control member that includes a mean to change the volume of the actuator chamber. All the units such as optical element, actuator with tubing and control member are placed and protected inside holder 1070 which is detachably attached to the carrier 1055. The carrier 1055 also include trench channel 1080 at its front surface running from the optical element to the edge of the carrier 1055 if the conversion is conducted at the back surface of single focus eyewear lens. Left CS 1060 is of the same construction and includes carrier 1065 with detachably attached holder 1075 to maintain and protect corresponding optical element, actuator with tubing connected to the optical element and control member inside. It also includes trench channel at the same surface.

The method of MVC of single focus lens 1030 involves (a) edging the carrier 1055 into carrier 1055' for the frame 1030 for fitting onto the back of the right lens 1030 with proper orientation for the trench channel towards right end piece of the frame 1020, (b) making a cut-out at the end of trench channel at the edge of the carrier 1055', (c) detaching the holder 1070 to release the protected elements, (d) attaching the actuator and control member at the back side of the carrier 1055' with tubing connecting the optical element and actuator to position at the trench channel and through the cut-out at the end of the trench channel, and (e) assembling the currier 1055' with the lens 1030 by bonding carrier 1055' front surface onto the back surface of the lens 1030. The same method of MVC is performed for the left lens 1040 by the left CS 1060 where the left carrier 1065 is edged into carrier 1065' with the orientation of the trench channel towards left piece of the frame 1020.

FIG. 8C demonstrates the resulted Multi Viewing Eyewear 1010' as the result of MVC of both single focus eyewear lenses 1030 and 1040. The conversion preserves the original frame 1020 of the Eyewear 1010 to allow for a wearer to choose any frame of preference. It also preserves refraction of each single focus lenses 1030 and 1040 called refraction members. The result of MVC is right multi-viewing lens 1030' and left multi-viewing lens 1040'. For instance, as the assembly of lens 1030 and carrier 1055' at the back surface of the lens 1030 results in SBS optical element 1090 securing between them. Thus, the actuator 1100 is attached at the back of the carrier 1055' and, therefore, back of the lens 1030' near the right end piece 1025. The tubing 1110 connecting the SBS optical element 1090 and actuator 1100 is secure at the trench channel 1080. It can be secured by an adhesive with the refractive index matching the refractive index of the carrier material in order to make the connection between the actuator 1100 and SBS optical element 1090 optically invisible. The control member represents in this case by the control lever 1120 for a manual control a volume of the actuator fluidic chamber for switching between different power levels as explains previously by FIG. 4A though FIG. 5B. The control lever 1120 is also attached at the back surface of the lens 1030' for easy access by the wearer and having a minimum visibility from the outside. The same description is applied to left lens 1040' having SBS optical element 1090' between the carrier 1065' and lens 1040 attached to the actuator 1100' by tubing 1110'.

Control member of a conversion system may be an electronic control member that uses touch or inductive control to manage the actuator for switching SBS optical element. An optical element may be a different type as listed above—fluidic optical element with a surface shape change, Alvarez design lens with movable wave plate or material-based switching optical element. Instead of tubing, a wiring would be placed at the trench channel connecting control member and an electronically controlled optical element such as material-based switchable optical element.

Figure 9:
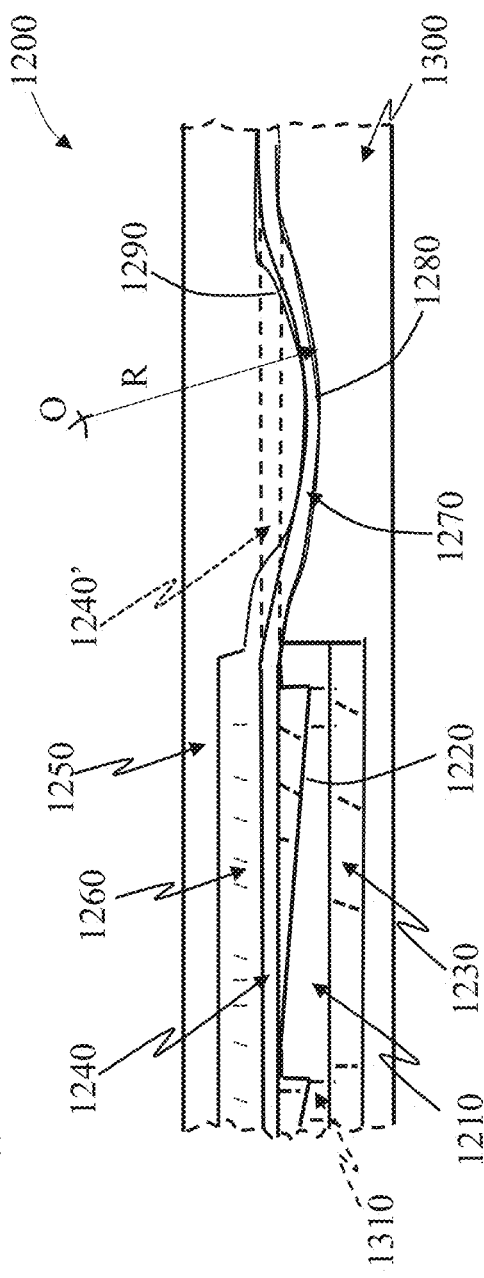
FIG. 9 demonstrates a peripheral cross-section of a multi-chamber switchable optical element to control elastic membrane radial strain.

FIG. 9 demonstrates an example of a design to control a radial stress of the membrane of a switchable optical element. The optical element design might be either of one described on FIG. 4B and FIG. 5B. FIG. 9 shows a section 1200 of cross-section of a switchable optical element periphery that includes optical substrate 1210 and a part where the membrane 1240 is bonded to the substrate support 1300 (or substrate itself) at one side and membrane cover 1250 at the other side. Substrate cover 1300 includes circular trench channel 1280 around the optical substrate 1210. The trench channel has a radius R with the center O, though the trench channel could be a different shape. The membrane 1240 is attached to a periphery of the substrate cover 1300 outside the trench channel 1280 as shown of the continuation of flat shape 1240' at the trench channel 1280. The optical element might be a curved shape. The membrane might be in contact with substrate cover 1210 at the side of the guiding surface 1220 forming active chamber with the optical substrate connected with the internal chamber 1230 via through channel 1310 and so on. As the membrane is placed over the substrate 1210 and bonded to the substrate cover 1300 outside the trench channel. The membrane cover 1250 is also attached to the membrane 1240 outside the trench channel location. The membrane cover 1250 includes circular elevation of curvature 1290 that compliments a shape of the trench channel 1280 at the substrate cover 1300. The placement of the membrane cover 1250 then presses the part of the membrane 1240' over the trench channel 1280 against the trench channel into shape 1270 thus creating a radial tension of the membrane 1240 by stretching the membrane 1240 radially. A magnitude of stretching depends on a shape of the trench channel 1280—longer its arc length is, larger a radial strain of the membrane would be. A trench channel can be placed at the membrane cover instead, with membrane first bonded to its periphery and then the substrate cover with the complimented to the trench channel shape is attached for radial stretching of the membrane.

FIG. 10 demonstrates the way to provide 3 foci by SBS OE that includes intermediate focus in addition to far and near foci by applying synchronization method. FIG. 10 demonstrates a part of section 1150 of SBS optical element analogous to one shown on FIG. 2 with single focus diffractive guiding surface. The synchronization method application to SBS OE is performed on the example with matching fluid being placed at the active chamber as the preferred embodiment but it is not limited to this configuration. The SBS OE is represented by section 1150 produces near focus when SBS OE is in diffractive state with membrane taking diffractive form of conforming to the diffractive guiding surface 1160. Thus, the section 1150 includes optical substrate 1160 and membrane 1200 forming active chamber 1210 filled with matching optical fluid connected with internal chamber 1190 by through channels 1220, 1220' and so on. The internal chamber 1190 is formed between the optical substrate 1160 and substrate support 1180. The diffractive guiding surface 1170 is blazed shape which is also called relief. A periodicity of relief is defined by the groove periods $L_{near1}$, $L_{near2}$ and so on of the diffractive guiding surface 1170 to create near focus at a certain Add power.

FIG. 11 demonstrates relief 1220 that is synchronized with diffractive guiding surface 1170. Similar to the relief 1170 of FIG. 10 is also circular shaped. It has larger periods as one designated as $L_{int}$, which is synchronized with the periods of the diffractive relief 1170 such that the ratio of larger period to corresponding smaller period in $r^2$ coordinates at the same radius is an integer N=2. For instance, in comparing relief profile of 1220 and profile of the diffractive guiding surface 1170, the ratio $L_{int}/(L_{near1}+L_{near2})=2$. The same synchronization is applied to other periods of the relief 1220.

FIG. 12 demonstrates section 1250 of SBS optical element where the diffractive guiding surface 1270 is the synchronized combination of reliefs 1170 and 1270 and is called "synchronized guiding surface". The component with periods $L_{near1}$, $L_{near2}$ and so on of smaller periods relief of the synchronized guiding surface 1170 produces larger Add power for near focus and the component with larger periods $L_{int}$ and so on produces smaller Add power which is half of the larger Add power and suitable for intermediate focus. The section 1250 also includes optical substrate 1260 with synchronized diffractive guiding surface 1270, membrane 1300 to form active chamber 1310 filled with matching optical fluid connected with the internal chamber 1290 via through channels 1320, 1320' and so on. The internal chamber 1290 is formed between the optical substrate 1260 and substrate support 1280. As the fluid is removed from the active chamber 1310 into the internal chamber 1290, the membrane 1300 shown in refractive form takes the diffractive form of the synchronized diffractive guiding surface 1270 to manifest synchronized combination of two reliefs with ratio of their periods in $r^2$ coordinate equals N=2, i.e. two Add powers, one for near focus and another for intermediate focus. Thus, it is desirable that the original relief 1170 manifest the grooved height to produce single focus image at the $1^{st}$ order focus and the relief manifest periodicity to produce Add power $AP_1$, say for near, the synchronized relief 1220 with N=2 may also has groove height to produce single focus image at $1^{st}$ order focus and its periodicity is set by synchronization with N=2 thus to produce Add power $AP_2=AP_1/2$. The synchronized diffractive guiding surface thus produces two $1^{st}$ order foci, i.e. light split between them, with Add powers of $AP_1$ for near focus and $AP_2$ for intermediate focus. For instance, if $AP_1$=3 D, then $AP_2$=1.5 D. Thus, the corresponding SBS OE with the diffractive guiding surface being a synchronized combination of two reliefs with the ratio of their periods in $r^2$ coordinates equals N=2, switches between single focus refractive state for far and bifocal diffractive state for near and intermediate.

In general. The ratio of synchronized large period to small period of two reliefs can be N>1 with resulted smaller Add power $AP_N=AP/N$, where AP is larger Add power. For instance, synchronization with N=3 means that 3 smaller periods of one relief overlap with one larger period of another relief, and Add power produced by the relief with smaller periods is AP, the Add power produced by the relief with larger period is $AP_3=AP/N$. For instance, is AP=3 then $AP_3$=1 D.

Thus, first step is to select a relief with periodicity to place first order focus for near viewing, about 3 D add counted from an optical power of the refractive state. The groove height to act as a kinoform or multimode diffractive surface for single focus performance, say, 100% of light is directed to the first diffractive order. Then to select a relief with larger period according to the synchronization method to produce first order focus at the Add power that is smaller the Add power of the first relief. Its groove height is also to direct 100% light to the first order focus for this relief. The combined synchronized diffractive surface becomes the diffractive guiding surface that splits light between two first orders diffractive foci of the original reliefs, one for near and another for intermediate viewing. The resulted SBS optical element switches between single focus far focus in the refractive state and bifocal state with intermediate and near viewing in the diffractive state.

The fundamentals property of the synchronization method is to create a structure where foci of the relief with larger periods coincides with some foci of the relief of smaller periods. In the above example with N=2, the second order focus of the relief with lager periods coincides with first order of relief of smaller periods. In the example with N=3, the third order focus of the relief of smaller periods coincides with first order focus of the relief with larger periods. In a generalized structure of the synchronized method two reliefs form synchronized structure where K order focus of the relief with larger periods coincides with K×N (N>1) focus of the relief with smaller periods.

FIGS. 13A through 16B describe a method of conversion of a single focus contact lens defined by its refraction and fitting characteristics into adjustable power contact lens between at least two different foci, for instance, far and near foci or far and intermediate foci. Similar to Eyewear lens it is also called Multi Viewing Conversion (MVC). The preferred embodiment is to conduct multi viewing conversion with SBS OE as active member for quick switching between foci where SBS OE is a multi-chamber construction described by FIGS. 4A and 4B or FIGS. 5A and 5B, but MVC is fully applicable to other active members with different mechanisms of optical power adjustable (fluidic balloon) or material based switchable contact lens. Thus, the MVC of contact lens to be demonstrated with the use of multi-chamber SBS optical element.

FIG. 13A shows a front view of the Conversion System 1350. It consists of surface based switchable optical element 1360 that includes guiding surface with multiple diffractive grooves 1370 with through holes spread out over each groove. The SBS OE 1360 is the active member of the conversion system 1350 and is to provide Add power to the contact lens by switching between foci. It is a standard element for the same Add power which helps with the cost of switchable contact lenses manufacturing. The conversion system 1350 also includes actuation 1380 with the actuator chamber filled with fluid 1400 for switching SBS OE between the foci. The actuator chamber 1400 is connected with SBS OE 1360 via channel 1410 with fluid 1420. A control member 1390 is a part of the actuator 1380 and represents a flexible wall that increase its strain with a pressure. This is a simple mechanical control member but it can be a pressure or bend sensor with electronic-power element to create an electric signal if a pressure is applied to the control member.

FIG. 13B represents a side view of the conversion system 1350 to demonstrate front surface 1440 and back surface 1430 of the switchable element 1360 with guiding surface 1370. A chamber of the SBS OE 1360 is connected by channel 1410 with the actuator chamber 1400. The bottom part of the actuator 1380 is the control member 1380 as explained above.

FIG. 14A demonstrates a front view of a refraction member 1450 to provide refraction correction within the optical zone 1460. The optical zone 1460 is surrounded by the transition zone 1470. The optical zone dimeter is about 7 mm. There is also a cut out 1480 at the back of the refraction member 1450 shaped to accept conversion system 1350.

FIG. 14B is a side view of the refraction member 1450. It includes a transition zone 1470 at the periphery and optical zone 1460 at the middle with front surface 1490 to provide necessary sphero-cylinder correction and back surface 1490 to provide base surface of converted contact lens. Refraction member 1460 is a standard element for a given refraction correction of a switchable contact lens to help to keep cost down for switchable contact lenses manufacturing. The cut out 1480 serves for placement of the conversion system 1350 at the back of the refraction member 1450. A curvature of the back surface 1490 of the refraction member 1460 is the same as the curvature of the back surface 1430 of the active member 1360 to provide base surface of resulted switchable contact lens. A refraction member is made of soft material or gas permeable material commonly used for contact lenses to provide gas exchange with the cornea.

FIG. 15A demonstrates a front view of a base member 1520 of switchable contact lens. It is analogous to a frame as the base member of a switchable Eyewear disclosed above. The base member includes lenticular portion 1530 of a switchable contact lens for fitting the lens over the cornea. The internal diameter of the lenticular portion is such to allow placement of the refraction member 1450 within the internal diameter of the lenticular portion 1530. For this purpose, the lenticular portion includes cuts out 1550 for actuation 1380 placement. The space within the lenticular portion 1530 can be an opening for refraction member placement. In this case the back surface of the assembled switchable lens is cut upon the lens assembly in order to produce a smooth transition between back surface of the lenticular portion, refraction member and active member. A preferable option is to include a very thin sheet of material within the internal diameter of the lenticular portion 1530 that is also a single piece with the lenticular portion 1530 of the lenticular portion 1530 to provide continuous and smooth back surface over the whole back surface of the switchable contact lens 1580. In this case, the refraction member is bonded to the front surface of the thin sheet within the internal diameter of the lenticular portion 1530. The lenticular portion and thin sheet are made of soft material such as silicone, hydrogel or silicone hydrogel type commonly used by contact lenses.

FIG. 15B is a side view of the base member 1520 to demonstrate lenticular portion 1530 and thin sheet of material 1540 shaped for its front surface 1560 to be equivalent to a curvature of the back surfaces 1430 and 1490 of refraction member and active to result in smooth and continuous base surface of switchable contact lens to avoid any corneal abrasion. A thickness of the thin sheet is in the order of tens of microns.

FIG. 16A demonstrates a front view of switchable contact lens 1580 as the assembly of the conversion system 1350, refraction member 1450 and base member 1520. It shows the locations of the lenticular portion (contact lens soft skirt) 1530, optical zone 1460 of the refraction member 1450 with the transition 1470 to the lenticular portion 1530, active member 1360 with SBS optical element 1370 connected to the actuator 1380. Actuator 1380 includes control unit 1390 in the form of its bottom surface of certain mechanical properties that increase strain with applied pressure. It is shown in a shape without applied pressure and shape 1390' if applied pressure. In the latter case, the volume of the actuator chamber is reduced to push some fluid from the actuator chamber into the SBS optical element 1370 for switching to a higher optical power.

FIG. 16B demonstrates a side view of the switchable contact lens (SCL) 1580. It shows the refraction member placement against base member with the transition zone 1470 transitioning refractive member to the lenticular portion 1530. It also shows front surface 1560 of the base member 1520 placement against back surface 1490 of the refraction member 1450 with back surface 1570 becoming the base surface of the switchable contact lens 1580. The total thickness of the switchable contact lens 1580 can be around 150 microns. The actuator 1380 serves as the ballast of the contact lens 1580 to maintain its orientation on the eye with the ballast staying at the bottom of the contact lens 1580. This allows for interaction of the control member 1390 with the lower eyelid as well as a proper cylinder orientation of the refraction member for eye astigmatism correction. It is also shown bottom part of the actuator (ballast) 1380 with the control member 1390 without an applied pressure and shape 1390' with the applied pressure. The pressure is applied by the lower eyelid with the wearer of the switchable contact lens 1580 looking down for near viewing. A volume of the actuator chamber reduces pushing some fluid into SBS optical element for switching to near focus. A simple mechanical control member is demonstrated but it could be replaced by a pressure switch for electronic control in a material based switching, for instance. The active member might also be a balloon type design to change volume with the fluid increase in the balloon when the fluid is squeezed out from the actuator chamber upon the low eyelid pressure.

What is claimed is:

1. A switchable optical element, comprising:
an optical substrate on a first side having a plurality of diffractive grooves forming a diffractive guiding surface;
an elastic membrane disposed adjacent to the first side of the optical substrate and configured to be movable in contact with the diffractive guiding surface;
wherein the elastic membrane and the optical substrate form an active chamber there between, the active chamber defining a plurality of sections where each section is formed over each diffractive groove of the plurality groove and having a variable depth between the elastic membrane and the optical substrate;
a substrate cover disposed adjacent to a second side of the optical substrate, the second side being opposite the first side;
wherein the substrate cover and the optical substrate form an internal chamber there between;
wherein in a first state a first optical fluid fills each plurality of sections of the active chamber;
wherein in a second state the first optical fluid is removed from each plurality of sections of the active chamber and flows to the internal chamber through a plurality of channels perpendicularly disposed through the optical substrate fluidically connecting the active and internal chambers; and
wherein in the second state the elastic membrane is configured to conform to the plurality of diffractive grooves of the diffractive guiding surface with the periodicity of the diffractive guiding surface.

2. The switchable optical element of claim 1, wherein the plurality of channels are located respectively at their deepest portion of their variable depth for each diffractive groove.

3. The switchable optical element of claim 1, wherein the first optical fluid is a matching fluid to the optical substrate, a refractive index of the first optical fluid being equal to or close to a refractive index of the optical substrate.

4. The switchable optical element of claim 1, wherein the first optical fluid is a non-matching fluid to the optical substrate, a refractive index of the first optical fluid being different to a refractive index of the optical substrate.

5. The switchable optical element of claim 1, including a membrane cover disposed adjacent to the elastic membrane on an opposite side in comparison to the active chamber, wherein the membrane cover and the elastic membrane form an external chamber there between, wherein a second optical fluid fills the external chamber.

6. The switchable optical element of claim 5, wherein the first optical fluid is of an opposite matching or non-matching fluid in comparison to the second optical fluid.

7. The switchable optical element of claim 5, wherein the first optical fluid and the second optical fluid do not have the same refractive index.

8. The switchable optical element of claim 5, wherein the membrane cover comprises an additional optical characteristic being an asphericity or a bi-asphericity.

9. The switchable optical element of claim 5, wherein the membrane cover comprises an additional optical characteristic being an asphericity or a bi-asphericity, and wherein the optical substrate comprises an additional optical characteristic being an extended depth of focus at near foci or intermediate foci.

10. The switchable optical element of claim 5, wherein a gas-filled accumulator pocket is formed in the substrate cover sealed by a portion of the elastic membrane, wherein a portion of the second optical fluid is disposed adjacent the gas-filled accumulator pocket on an opposite side of the portion of the elastic membrane.

11. The switchable optical element of claim 5, wherein a gas-filled accumulator pocket is formed in the membrane cover sealed by a portion of the elastic membrane, wherein a portion of the first optical fluid is disposed adjacent the gas-filled accumulator pocket on an opposite side of the portion of the elastic membrane.

12. The switchable optical element of claim 5, including an actuator connector in fluidic communication with the second optical fluid, wherein the actuator connector is configured to connect to a means for transporting the second optical fluid in or out of the external chamber to select between the first and second states.

13. The switchable optical element of claim 1, wherein the optical substrate comprises an additional optical characteristic being an extended depth of focus at near foci or intermediate foci.

14. The switchable optical element of claim 1, including an actuator connector in fluidic communication with the first optical fluid, wherein the actuator connector is configured to connect to a means for transporting the first optical fluid in or out of the active chamber to select between the first and second states.

15. A switchable optical element, comprising:
an optical substrate on a first side forming a guiding surface;
an elastic membrane disposed adjacent to the first side of the optical substrate and configured to be movable in contact with the guiding surface;
wherein the elastic membrane and the optical substrate form an active chamber there between, the active chamber having a variable depth between the elastic membrane and the optical substrate;
a substrate cover disposed adjacent to a second side of the optical substrate, the second side being opposite the first side;
wherein the substrate cover and the optical substrate form an internal chamber there between;
wherein in a first state a first optical fluid fills the active chamber;
wherein in a second state the first optical fluid is removed from the active chamber and flows to the internal chamber through a plurality of channels perpendicularly disposed through the optical substrate fluidically connecting the active and internal chambers, wherein the plurality of channels are located respectively at their deepest portion of their variable depth of the guiding surface;
wherein in the second state the elastic membrane is configured to conform to the guiding surface shape; and
a membrane cover disposed adjacent to the elastic membrane on an opposite side in comparison to the active chamber, wherein the membrane cover and the elastic membrane form an external chamber there between, wherein a second optical fluid fills the external chamber.

16. The switchable optical element of claim 15, wherein the first optical fluid is a matching fluid to the optical substrate, a refractive index of the first optical fluid being equal to or close to a refractive index of the optical substrate, or, wherein the first optical fluid is a non-matching fluid to the optical substrate, a refractive index of the first optical fluid being different to a refractive index of the optical substrate, and wherein the first optical fluid is of an opposite matching or non-matching fluid in comparison to the second optical fluid.

17. The switchable optical element of claim 16, wherein the membrane cover comprises an additional optical characteristic being an asphericity or a bi-asphericity, and/or wherein the optical substrate comprises an additional optical characteristic being an extended depth of focus at near foci or intermediate foci.

18. The switchable optical element of claim 15, wherein the guiding surface is a diffractive guiding surface or a refractive guiding surface.

19. A switchable optical element, comprising:
an optical substrate on a first side having a plurality of diffractive grooves forming a diffractive guiding surface;
an elastic membrane disposed adjacent to the first side of the optical substrate and configured to be movable in contact with the diffractive guiding surface;
wherein the elastic membrane and the optical substrate form an active chamber there between, the active chamber defining a plurality of sections where each section is formed over each diffractive groove of the plurality groove and having a variable depth between the elastic membrane and the optical substrate;
a substrate cover disposed adjacent to a second side of the optical substrate, the second side being opposite the first side;
wherein the substrate cover and the optical substrate form an internal chamber there between;
wherein in a first state a first optical fluid fills each plurality of sections of the active chamber;
wherein in a second state the first optical fluid is removed from each plurality of sections of the active chamber and flows to the internal chamber through a plurality of channels perpendicularly disposed through the optical substrate fluidically connecting the active and internal chambers, wherein the plurality of channels are located respectively at their deepest portion of their variable depth for each diffractive groove;
wherein in the second state the elastic membrane is configured to conform to the plurality of diffractive grooves of the diffractive guiding surface with the periodicity of the diffractive guiding surface;
a membrane cover disposed adjacent to the elastic membrane on an opposite side in comparison to the active chamber, wherein the membrane cover and the elastic membrane form an external chamber there between, wherein a second optical fluid fills the external chamber;
a gas-filled accumulator pocket formed either in:
the substrate cover sealed by a portion of the elastic membrane, wherein a portion of the second optical fluid is disposed adjacent the gas-filled accumulator pocket on an opposite side of the portion of the elastic membrane; or the membrane cover sealed by a portion of the elastic membrane, wherein a portion of the first optical fluid is disposed adjacent the gas-filled accumulator pocket on an opposite side of the portion of the elastic membrane; and an actuator connector in fluidic communication with the first optical fluid, wherein the actuator connector is configured to connect to a means for transporting the first optical fluid in or out of the active chamber to select between the first and second states.

20. The switchable optical element of claim 19, wherein the first optical fluid is a matching fluid to the optical substrate, a refractive index of the first optical fluid being equal to or close to a refractive index of the optical substrate, or, wherein the first optical fluid is a non-matching fluid to the optical substrate, a refractive index of the first optical fluid being different to a refractive index of the optical substrate, and wherein the first optical fluid is of an opposite matching or non-matching fluid in comparison to the second optical fluid.

21. The switchable optical element of claim 20, wherein the membrane cover comprises an additional optical characteristic being an asphericity or a bi-asphericity, and/or wherein the optical substrate comprises an additional optical characteristic being an extended depth of focus at near foci or intermediate foci.

\* \* \* \* \*